US010912853B2

(12) United States Patent
Blattner et al.

(10) Patent No.: US 10,912,853 B2
(45) Date of Patent: *Feb. 9, 2021

(54) SOLID AIR FRESHENER

(71) Applicant: Ecolab USA Inc., Saint Paul, MN (US)

(72) Inventors: Amanda Ruth Blattner, Saint Paul, MN (US); Charles Allen Hodge, Saint Paul, MN (US); Timothy John Kohnke, Saint Paul, MN (US); Mark Dennis Levitt, Saint Paul, MN (US); Julie E. Marquardt, Saint Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 84 days.

This patent is subject to a terminal disclaimer.

(21) Appl. No.: 16/233,298

(22) Filed: Dec. 27, 2018

(65) Prior Publication Data
US 2019/0125913 A1 May 2, 2019

Related U.S. Application Data

(63) Continuation of application No. 15/608,659, filed on May 30, 2017, now Pat. No. 10,201,627, which is a continuation of application No. 15/221,351, filed on Jul. 27, 2016, now Pat. No. 9,782,508, which is a continuation of application No. 14/564,663, filed on Dec. 9, 2014, now Pat. No. 9,402,930, which is a continuation of application No. 13/302,570, filed on Nov. 22, 2011, now abandoned.

(51) Int. Cl.
A61L 9/01 (2006.01)
A61L 9/04 (2006.01)
A01M 1/20 (2006.01)
B05B 7/24 (2006.01)
A61L 9/05 (2006.01)
A61L 9/12 (2006.01)

(52) U.S. Cl.
CPC ............ A61L 9/01 (2013.01); A01M 1/2055 (2013.01); A61L 9/042 (2013.01); A61L 9/048 (2013.01); A61L 9/05 (2013.01); A61L 9/12 (2013.01); B05B 7/2408 (2013.01)

(58) Field of Classification Search
CPC . A61L 9/12; A61L 9/042; A61L 9/048; A61L 9/01; A61L 9/05; A01M 1/2055; B05B 7/2408; B05B 11/3011
USPC ...... 239/6, 34, 60, 302, 333; 424/76.1, 76.3, 424/76.4; 512/1
See application file for complete search history.

(56) References Cited

U.S. PATENT DOCUMENTS

| 4,056,612 A | 11/1977 | Lin |
| 4,226,944 A | 10/1980 | Stone |
| 4,666,671 A | 5/1987 | Purzycki et al. |
| 5,723,420 A | 3/1998 | Wei et al. |
| 6,009,567 A | 1/2000 | Dean et al. |
| 6,036,964 A | 3/2000 | Guenin et al. |
| 6,083,456 A | 7/2000 | Van Rees |
| 6,110,886 A | 8/2000 | Scepanski |
| 6,180,092 B1 | 1/2001 | Lagin |
| 6,254,823 B1 | 7/2001 | Rees |
| 6,328,951 B1 | 12/2001 | White et al. |
| 6,403,186 B1 | 6/2002 | Tararuj et al. |
| 6,451,746 B1 | 9/2002 | Moore et al. |
| 7,183,249 B2 | 2/2007 | Dente |
| 7,202,201 B1 * | 4/2007 | Williams .................. A61L 9/01 512/1 |
| 7,485,610 B2 | 2/2009 | Heinz et al. |
| 7,754,198 B2 | 7/2010 | Whitehead et al. |
| 8,343,521 B2 | 1/2013 | Shick et al. |
| 9,402,930 B2 | 8/2016 | Blattner |
| 2002/0127137 A1 | 9/2002 | Scepanski |
| 2002/0127813 A1 | 9/2002 | Scepanski |
| 2004/0202632 A1 | 10/2004 | Gott et al. |
| 2005/0227905 A1 | 10/2005 | Heinz et al. |
| 2007/0108759 A1 | 5/2007 | D'Amico |
| 2009/0257968 A1 | 10/2009 | Walton et al. |
| 2011/0318296 A1 | 12/2011 | Braun et al. |
| 2012/0091218 A1 | 4/2012 | Mikkelsen et al. |

FOREIGN PATENT DOCUMENTS

| WO | 9510216 | 4/1995 |
| WO | 9837171 | 8/1998 |
| WO | 2004006967 | 1/2004 |
| WO | 2004035721 | 4/2004 |
| WO | 2004105811 | 12/2004 |
| WO | 2006132863 | 12/2006 |

OTHER PUBLICATIONS

Chemia Corporation Material Safety Data Sheet, Product: Chemia TM #003047, (3 pages), dated. Aug. 6, 2010.
Lambent Technologies Corp. Material Safety Data Sheet, Product: Lumulse TM 1820, (3 pages), dated Aug. 22, 2003.
Lambent Technologies Corp. Material Safety Data Sheet, Product: Lumulse TM POE-40 MS KP, (3 pages), dated Aug. 22, 2003.
Lambent Technologies Corp. Material Safety Data Sheet, Product: Lumulse POE-100 MS, (3 pages), dated Aug. 22, 2003.

(Continued)

Primary Examiner — Steven J Ganey
(74) Attorney, Agent, or Firm — McKee, Voorhees & Sease, PLC

(57) ABSTRACT

The present invention relates to a solid pressed air freshener and odor neutralizer composition which can include greater than 10% fragrance. The air freshener comprises a fragrance; preferably the fragrance is impregnated within a water soluble substrate made from a foamed vegetable starch, a surfactant and a solidifier. The solid formulations break down easily in the presence of water and may be sprayed, within the area to be freshened.

18 Claims, No Drawings

(56) References Cited

OTHER PUBLICATIONS

Lambent Technologies Corp., Technical Data Sheet, Lumulse TM POE (100) MS, date unknown, (1 page). Jan. 1, 2016.
Lambent Technologies Corp., Technical Data Sheet, Lumulse TM POE (4), MS KP, date unknown (1 page). Jan. 1, 2016.
Lambent Technologies Corp., Technical Data Sheet, Lumulse TM 1804 and Lumulse 1820, 1102-24-1, date unknown, (2 pages). Jan. 1, 2016.

* cited by examiner

SOLID AIR FRESHENER

CROSS REFERENCE TO RELATED APPLICATIONS

This is a Continuation Application of U.S. Ser. No. 15/608,659 filed May 30, 2017, which is a Continuation Application of U.S. Ser. No. 15/221,351 filed Jul. 27, 2016, now U.S. Pat. No. 9,782,508, issued Oct. 10, 2017, which is a Continuation Application of U.S. Ser. No. 14/564,663 filed Dec. 9, 2014, now U.S. Pat. No. 9,402,930, issued Aug. 2, 2016, which is a Continuation Application of abandoned U.S. Ser. No. 13,302,570 filed Nov. 22, 2011. The entire contents of this patent application are hereby expressly incorporated herein by reference including, without limitation, the specification, claims, and abstract, as well as any figures, tables, or drawings thereof.

FIELD OF THE INVENTION

This invention relates to air fresheners and deodorizers and, in particular, this invention relates to water soluble air fresheners and room deodorizers in concentrated solid pressed formulations that are diluted on site by the customer to yield a liquid composition for use in domestic, institutional and/or industrial applications.

BACKGROUND OF THE INVENTION

Various types of air fresheners have been made to dispense fragrances and scents to mask or neutralize unpleasant odors or to simply provide a pleasant scent in a volume of air. One type of air freshener involves dissolving a fragrance in a liquid carrier, such as ethanol, isopropanol, or some other volatile organic compound. Fragrances may also be dissolved in water, although it is often necessary to use a surfactant or other emulsifying agent to dissolve the fragrance in water. The fragrance evaporates with the carrier, scenting the air.

Solid form fragrances are more desirable for products such as air-freshener used in rooms and automobiles. Diluting the concentrated solid air freshener at the point of use or at an intermediate location to form a liquid reduces the cost and space required to transport and store the air freshener. Thus it can be seen, there is a continuing need for solid water soluble air fresheners to be diluted by the customer on site to yield a liquid composition and to provide long lasting fragrance by incorporating as much perfume or fragrance as possible.

It is an object of the present invention to provide a solid air freshener formulation that is easy to manufacture and does not require high temperature casting.

It is another object of the invention to provide a solid air freshener formulation that includes greater than 10% fragrance.

It is yet another object of the invention to provide a solid air freshener that is stable and does not experience significant fragrance weeping across normal transportation temperatures of up to 30-50° C.

It is yet another object of the present invention to provide a solid air freshener that is easily dissolvable in water, and creates a clear liquid composition that is free of large particles and clumps.

Other objects, aspects and advantages of this invention will be apparent to one skilled in the art in view of the following disclosure, the drawings, and the appended claims.

SUMMARY OF THE INVENTION

This invention relates to air fresheners, odor masks and malodor neutralizers and, in particular, to a solid air freshener for reduction in transportation costs and for easy spray application upon dissolution and formation of a liquid composition.

The present invention relates to a solid air freshener and odor neutralizer and the method of manufacturing the improved air freshener. Generally, the air freshener, according to the present invention, comprises a fragrance, a surfactant and a solidifier, the fragrance is preferably impregnated within a starch substrate or admixed with a powder carrier such as sodium lauryl sulfate. Applicants have identified compositions which can be formed to solids by pressing techniques and which can stably include greater than 10% fragrance.

The solid formulations break down easily in the presence of water to form a liquid composition and then may be sprayed within the volume of air to be freshened. This saves on transportation costs as the solid may be formulated into the liquid composition at the point of use rather than at the manufacturing site.

This invention provides a substantially solid pressed composition for controlling odors once diluted into the liquid composition. The solid composition includes a fragrance component and preferably a starch or sodium lauryl sulfate carrier in combination with surfactant/solidifier component. The surfactant/solidifier may be the same or different compounds. According to the invention the air freshener includes a fragrance component of from about 40% by weight to about 80% by weight of the composition and a surfactant/solidifier component which comprises from about 20% by weight to about 60% by weight of the composition. In some preferred embodiments the surfactant/solidifier is each present in a ratio greater than about 1:1, preferably 5:1. Additional components may include viscosity modifiers, and/or solubility modifiers such as disintegration or dissolution aids, coupler compounds to bring the fragrance to solution, a high temperature stabilizer, an effervescence dissolution combination, deodorizers, dyes, colorants and the like. The present invention also includes an article of manufacture, the article of manufacture including the above-referenced substantially solid pressed composition in a container.

The present invention further provides a method of making a solid composition by extrusion, pressing or any other means. The method of the present invention can produce a stable solid with reduced leaching of fragrance without employing a melt and solidification of the melt as in conventional casting. Forming a melt requires the expense of heating a composition to melt it as well as safety issues of handling a hot melt. In contrast, the present method can employ ambient temperature and humidity during solidification. The solids of the present invention are held together not by solidification from a melt but by binding through compression.

The present invention also includes a method for deodorizing/freshening a surface, bounded volume of air, or environment. The method include dissolving the solid pressed air freshener to form a liquid composition, and applying the liquid solution to the surface, bounded volume of air, or environment to eliminate or attenuate odors.

The present invention may further provide a method of applying a predetermined concentration of a deodorizing solution for eliminating or attenuating odors.

Additional objects, advantages, and features of various embodiments of this invention will be set forth in part in the description which follows, and in part will become apparent to those skilled in the art upon examination of the following, or may be learned by practice of the invention. The objects and advantages of various embodiments of this invention may be realized and attained by means of the instrumentalities and combinations particularly pointed out in the appended claims. Thus, these and other objects, features, and advantages of this invention will become apparent to a person of ordinary skill in the art from the description which follows.

DETAILED DESCRIPTION OF THE PREFERRED EMBODIMENT

While the presently described technology will be described in connection with one or more preferred embodiments, it will be understood by those skilled in the art that the technology is not limited to only those particular embodiments. To the contrary, the presently described technology includes all alternatives, modifications, and equivalents as may be included within the spirit and scope of the appended claims.

The term "solid" is defined as an essentially homogeneous dispersion, which is nonflowable at room temperature (e.g., 68° F. (20° C.)). Embodiments of the solid of this invention may have a melting point of at least about 37.7° C. (100° F.), at least about 45° C. (113° F.), or at least about 52° C. (125° F.). A substantially solid composition is one which does not exit a container when the open container is inverted (when the container opening is downwardly oriented). The present substantially solid composition is also distinguished from a composition which, while solid, is powdered, particulate, or granular in that it will not exit an opened, inverted container as opposed to the former products, which are free-flowing and are not consolidated in one discrete mass. In one aspect, the present substantially solid pressed products are made by pressing dry ingredients and an optional binder in a mold. Subsequently, the present substantially solid composition can be dispensed from within these containers. However, the present substantially solid composition can be removed from the molds after hardening and then dispensed without the use of these containers as well.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, "weight percent," "wt. %," "percent by weight," "% by weight," and variations thereof refer to the concentration of a substance as the weight of that substance divided by the total weight of the composition and multiplied by 100. It is understood that, as used here, "percent," "%," and the like are intended to be synonymous with "weight percent," "wt. %," etc.

The term "about," as used herein, modifying the quantity of an ingredient in the compositions of the invention or employed in the methods of the invention refers to variation in the numerical quantity that can occur, for example, through typical measuring and liquid handling procedures used for making concentrates or use solutions; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about," the claims include equivalents to the quantities. All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers subsumed within that range (e.g. 1 to 5 includes 1, 1.5, 2, 2.75, 3, 3.80, 4, and 5).

Compositions of the Invention

The present substantially solid pressed composition may include: a fragrance component, optionally with a starch or surfactant carrier, in combination with a surfactant and solidifier and optional ingredients to, e.g., modify the viscosity of the composition or modify the solubility of the use solution, such as disintegration or dissolution aids, coupler compounds to bring the fragrance into solution, a high temperature stabilizer, an effervescence dissolution combination, and the like. The surfactant and solidifier may be the same or different compounds. According to the invention a pressed air freshener is disclosed which includes a fragrance component of from about 40% by weight to about 80% by weight of the composition and the surfactant and solid air freshening composition comprise from about 20% by weight to about 60% by weight of the composition.

Fragrance

The present solid air freshening composition includes fragrances, which are pleasant smelling and which mask objectionable odors. Non-limiting examples of these fragrances include: Irish Spring™ fragrance (Intercontinental Fragrances), Lemon fragrance (Value Products), 9501 Non-acid Bathroom Cleaner Fragrance™ (Intercontinental Fragrances).

The solid pressed air fresheners of the invention can include greater than 10% fragrance. These fragrances may be present in amounts, by weight, of between about 10% and 35%, between about 10% and 30%, between about 10% and 25%, or any range subsumed therein. A person of ordinary skill in the art will appreciate that other suitable fragrances are readily available and may be utilized in the present invention without undue experimentation.

The fragrance and starch carrier are present in the invention in an amount from about 40% by weight to about 80% by weight of the pressed solid composition.

Surfactant

The solid air freshening composition of the invention can include a surfactant or surfactant system. A variety of surfactants can be used in a solid air freshening compositions, such as anionic, nonionic, cationic, and zwitterionic surfactants. Exemplary surfactants that can be used are commercially available from a number of sources. For a discussion of surfactants, see Kirk-Othmer, Encyclopedia of Chemical Technology, Third Edition, volume 8, pages 900-912.

Anionic surfactants useful in the solid air freshening composition includes, for example, carboxylates such as alkylcarboxylates (carboxylic acid salts) and polyalkoxycarboxylates, alcohol ethoxylate carboxylates, and the like; sulfonates such as alkylsulfonates, alkylbenzenesulfonates, alkylarylsulfonates, sulfonated fatty acid esters, and the like; sulfates such as sulfated alcohols, sulfated alcohol ethoxylates, sulfated alkylphenols, alkylsulfates, sulfosuccinates, alkylether sulfates, and the like; and phosphate esters such as alkylphosphate esters, and the like. Exemplary anionic surfactants include sodium alkylarylsulfonate, alpha-olefinsulfonate, and fatty alcohol sulfates.

Nonionic surfactants useful in the solid air freshening composition include, for example, those having a polyalkylene oxide polymer as a portion of the surfactant molecule. Such nonionic surfactants include, for example, chlorine-, benzyl-, methyl-, ethyl-, propyl-, butyl- and other like alkyl-capped polyethylene glycol ethers of fatty alcohols; polyalkylene oxide free nonionics such as alkyl polyglycosides; sorbitan and sucrose esters and their ethoxylates; alkoxylated ethylene diamine; alcohol alkoxylates such as alcohol ethoxylate propoxylates, alcohol propoxylates, alcohol propoxylate ethoxylate propoxylates, alcohol ethoxylate butoxylates, and the like; polyoxyethylene glycol ethers and the like; carboxylic acid esters such as glycerol esters, polyoxyethylene esters, ethoxylated and glycol esters of fatty acids, and the like; carboxylic amides such as diethanolamine condensates, monoalkanolamine condensates, polyoxyethylene fatty acid amides, and the like; and polyalkylene oxide block copolymers including an ethylene oxide/propylene oxide block copolymer such as those commercially available under the trademark PLURONIC® (BASF-Wyandotte), and the like; and other like nonionic compounds. Silicone surfactants such as the ABIL® B8852 can also be used.

Cationic surfactants that can be used in the solid air freshening composition include amines such as primary, secondary and tertiary monoamines with $C_{1-8}$ alkyl or alkenyl chains, ethoxylated alkylamines, alkoxylates of ethylenediamine, imidazoles such as a 1-(2-hydroxyethyl)-2-imidazoline, a 2-alkyl-1-(2-hydroxyethyl)-2-imidazoline, and the like; and quaternary ammonium salts, as for example, alkylquaternary ammonium chloride surfactants such as n-alkyl($C_{12}$-$C_{18}$)dimethylbenzyl ammonium chloride, n-tetradecyldimethylbenzylammonium chloride monohydrate, a naphthylene-substituted quaternary ammonium chloride such as dimethyl-1-naphthylmethylammonium chloride, and the like. The cationic surfactant can be used to provide sanitizing properties.

Zwitterionic surfactants that can be used in the solid air freshening composition include betaines, imidazolines, and propinates.

The surfactants are present in the composition in an amount of from about 20% by weight to about 50% by weight of the composition.

Solidifier

The composition also includes a solidifier. The solidifier can comprise from about 15% by weight to about 40% by weight of the composition. In some cases the solidifier is also the surfactant. Such as Tomadol® 25-20 or Tomadol 25-12® ethoxylated alcohol surfactants or those available from Lambent under the tradename Lumulse™. In this situation, the surfactant/solidifier is present in the solid composition at amounts of from about 20% by weight to about 80% by weight of the composition.

Suitable materials used as solidifiers include alkaline polyacrylate solutions, alkali soluble acrylic copolymer emulsions, PEG-100 stearate, stearamide MEA, paraffin, ozokerite and cetearyl alcohol, cellulose derivatives, polyvinyl methyl ether, polyurethane thickeners, polyethylene oxide, and natural gums (including, Guar Gum, GumArabic, Gum Karaya, alginates, casein). In a preferred embodiment the solidifier is polyethylene glycol. The polyethylene glycol may be substituted at one or both ends as described supra and has an average molecular weight of about 2000 to about 6500 (PEG 2000-PEG 6500), and preferably, has an average molecular weight ranging from about 3000 to about 5000. In general, the number appearing after the designation "PEG" (polyethylene glycol) indicates the average molecular weight, e.g. PEG 200 represents polyethylene glycol with an average molecular weight of about 200, etc.

Additional Functional Components

Additional functional components may also optionally be incorporated into the compositions of the invention and include viscosity modifiers, and/or solubility modifier such as disintegration or dissolution aids, coupler compounds to bring the fragrance to solution, a high temperature stabilizer, an effervescence dissolution combination, and the like.

Disintegration Aid

These substances, also known as "disintegrants" based on their action, increase their volume when water is added, whereupon first the intrinsic volume increases (swelling) on the one hand, while on the other hand a pressure can be created via the release of gases, causing the solid composition to disintegrate into smaller particles. Old familiar disintegration aids include, for example, carbonate/citric acid systems, but other organic acids may also be used. Swelling disintegration aids include, for example, synthetic polymers such as polyvinylpyrrolidone (PVP) or natural polymers and/or modified natural substances such as cellulose and starch and their derivatives, alginates or casein derivatives. Polyvinyl alcohol may be also be used as a disintegrant for the constituents of the solid. Disintegration aids, when used in the composition typically are present in amounts of 5% to 35 wt. %, preferably 10 to 30 wt. % and more preferably 15 to 25 wt. % of the solid cast composition.

Effervescent System

In addition, gas-evolving effervescent systems may preferably also be used according to invention. The gas-evolving effervescent system may consist of a single substance, which releases a gas on coming in contact with water. Of these compounds, magnesium peroxide should be mentioned in particular, because it releases oxygen on contact with water. However, preferred effervescent systems consist of at least two components, which react to form a gas, e.g., an alkali metal carbonate and/or bicarbonate and an acidifying agent suitable for releasing carbon dioxide from the alkali metal salts in aqueous solution. Examples of acidifying agents that release carbon dioxide from the alkali salts in aqueous solution include boric acid and alkali metal hydrogen sulfates, alkali metal dihydrogen phosphates and other inorganic salts. However, organic acidifying agents are preferred for use, citric acid being an especially preferred acidifying agent. Acidifying agents are preferably used in effervescent systems from the group of organic di-, tri- and oligocarboxylic acids and/or mixtures.

An effervescent system, when used in the composition typically are present in amounts of 10% to 40 wt. %, preferably 1 5 to 35 wt. % and more preferably 20 to 30 wt. % of the solid cast composition.

Coupling Agents

The solid cast composition may include one or more coupling agents for bringing the materials of the composition to solution. Some non-limiting examples of suitable coupling agents include propylene glycol esters, glycerol esters, polyoxyethylene glycerol esters, polyglycerol esters, sorbitan esters, polyoxyethylene sorbitan esters, polyoxyethylene-polyoxypropylene polymers, sulfonates, dioctyl sodium succinate, stearoyl lactylate, and complex esters such as acetylated, lactylated, citrated, succinhylated, or diacetyl tartarated glycerides. The coupling agent is preferably a sorbitan ester such as polyoxyethylene (20) sorbitan monooleate, commercially available as Polysorbate 80, polyoxyethylene (20) sorbitan monostearate, commercially available as Polysorbate 60, and polyoxyethylene (20) sorbitan monolaurate, commercially available as Polysorbate 20.

A coupling agent may be present in a concentration ranging generally from about 10 wt. % to about 40 wt. %, from about 15 wt. % to about 35 wt. %, and from about 20 wt. % to about 305 wt. %.

Temperature Stabilizer

Temperature stabilizers can be included to help prevent weeping of the fragrance at higher temperatures. Suitable temperature stabilizing agents include, for example linear or branched polycarboxylate polymers, especially polyacrylates. Inorganic temperature stabilizers including alumina, various clays, organo-modified clays, aluminates and silicates are also suitable. Temperature stabilizers may be present in an amount of from about 0.5 wt. % to about 40 wt. %, from about 1 wt. % to about 35 wt. %, and from about 5 wt. % to about 30 wt. %.

Deodorants

Deodorants may be incorporated in to the air freshener composition. These are substances which chemically alter odor producing substances. Non-limiting examples of deodorants include: 1. Bacterial spores, e.g., Sprozyme BCC™ (Semco Labs), 2. Enzymes, e.g., Vegetable Protein Concentrate A560™ (Carruba, Inc.), 3. Organic zinc compounds, e.g., Zinc ricinoleate, e.g., Tegosorb™, (Goldschmidt, AG), Zinc alkyl sulfates, Zinc alkylsulfonates, Zinc alkylarylsulfates, Zinc alkylarylsulfonates, Peroxides, e.g., hydrogen peroxide, Perborates, e.g., sodium perborate, Percarbonates, e.g., sodium percarbonate, Persulfates, e.g., sodium persulfate, Organic peroxides, e.g., Benzoyl peroxide, Dicumyl peroxide, and Di (2-tert-2-butyl peroxyisopropyl) benzene, Organic peroxyacids ($RCO_3H$), e.g., Peroxyformic acid, Peroxyacetic acid, Peroxybenzoic acid, and Metachloroperoxybenzoic acid, Meelium™ (Prentiss Drug and Chemical Co.), Cationic surfactants, e.g., quaternary ammonium salts, such as, Alkyldimethyl ammonium chloride, Alkyldimethylbenzyl ammonium chloride, and Alkyldimethylethylbenzyl amnonium chloride. These and other deodorants may be present in the substantially solid cast composition of this invention in an effective amount or in an amount between about 0.01% and 90%, between about 0.1% and 40%, between about 0.1% and 20%, between about 1% and 10%, or any range subsumed therein, by weight.

Optional ingredients are also contemplated to be within the scope of the present invention. These optional ingredients may include dyes such as (e.g., Pylakor Dark Violet Dye (Pylam Products)), mineral oil, water, alcohols, or glycols.

Methods of Making

In general the air freshener compositions are formed using a batch or continuous mixing system. In an exemplary embodiment, a single- or twin-screw extruder is used to combine and mix one or more components agents at high shear to form a homogeneous mixture. In some embodiments, the processing temperature is at or below the melting temperature of the components. The processed mixture may be dispensed from the mixer by pressing, forming, extruding or other suitable means, whereupon the composition hardens to a solid form. The structure of the matrix may be characterized according to its hardness, melting point, material distribution, crystal structure, and other like properties according to known methods in the art. Generally, a solid composition processed according to the method of the invention is substantially homogeneous with regard to the distribution of ingredients throughout its mass and is dimensionally stable.

Specifically, in a forming process, the liquid and solid components are introduced into the final mixing system and are continuously mixed until the components form a substantially homogeneous semi-solid mixture in which the components are distributed throughout its mass. In an exemplary embodiment, the components are mixed in the mixing system for at least approximately 5 seconds. The mixture is then discharged from the mixing system into, or through, a die, press or other shaping means. The product is then packaged. In an exemplary embodiment, the formed composition begins to harden to a solid form in between approximately 1 minute and approximately 3 hours. Particularly, the formed composition begins to harden to a solid form in between approximately 1 minute and approximately 2 hours. More particularly, the formed composition begins to harden to a solid form in between approximately 1 minute and approximately 20 minutes.

By the term "solid form", it is meant that the hardened composition will not flow and will substantially retain its shape under moderate stress or pressure or mere gravity. The degree of hardness of the composition may range from that of a fused solid product which is relatively dense and hard, for example, like concrete, to a consistency characterized as being a hardened paste. In addition, the term "solid" refers to the state of the composition under the expected conditions of storage and use of the solid composition. In general, it is expected that the composition will remain in solid form when exposed to temperatures of up to approximately 100° F. and particularly greater than approximately 120° F. with no or little leaching of fragrance.

The resulting solid composition may take forms including, but not limited to: an extruded, molded or formed solid pellet, block, tablet, powder, granule, flake; or the formed solid can thereafter be ground or formed into a powder, granule, or flake. In an exemplary embodiment, extruded pellet materials formed have a weight of between approximately 50 grams and approximately 250 grams, extruded solids have a weight of approximately 100 grams or greater, and solid blocks formed have a mass of between approximately 1 and approximately 10 kilograms. The solid compositions provide for a stabilized source of functional materials. In a preferred embodiment, the solid composition may be dissolved, for example, in an aqueous or other medium, to create a concentrated and/or use solution. The solution may be directed to a storage reservoir for later use and/or dilution, or may be applied directly to a point of use.

In other embodiments, the solid air freshener composition is provided in the form of a multiple-use solid, such as a block or a plurality of pellets, and can be repeatedly used to generate aqueous compositions for multiple uses. In certain embodiments, the solid air freshener composition is provided as a block, or a tablet having a mass between approximately 5 grams and approximately 10 kilograms. In certain embodiments, a multiple-use form of the solid composition has a mass between approximately 1 kilogram and approximately 10 kilograms. In further embodiments, a multiple-use form of the solid composition has a mass of between approximately 5 kilograms and about approximately 8 kilograms. In other embodiments, a multiple-use form of the solid composition has a mass of between about approximately 5 grams and approximately 1 kilogram, or between approximately 5 grams and approximately 500 grams.

The present invention provides a method for deodorizing/freshening a surface, bounded volume of air, or environment. The method may include providing the above-described deodorizing solution; and applying the deodorizing solution to the surface, bounded volume of air, or environment to eliminate or attenuate odors therein. In accordance with the present invention, a method is provided which includes the steps of applying water to the solid pressed air freshener so that the air freshener becomes dissolved to form a liquid composition, typically within a spray bottle, and directing a spray trigger nozzle generally at a surface, bounded volume of air, or environment, and spraying solution from the article.

| COMPOSITIONS | RANGE | PREFERRED | MORE PREFERRED |
| --- | --- | --- | --- |
| Fragrance/carrier | 40-80 | 45-75 | 50-70 |
| Surfactant | 20-50 | 25-45 | 30-40 |
| Solidifier | 15-40 | 20-35 | 25-30 |
| Disintegration aid | 0-35 | 0-30 | 0-25 |
| Effervescence | 0-40 | 0-35 | 0-30 |
| Coupler | 0-40 | 0-35 | 0-30 |
| High temp stabilizer | 0-40 | 0-35 | 0-30 |

The ratio of surfactant to solidifier is greater than 1:1, preferably 1:3 and more preferably 1:5. The surfactant may also be a solidifier.

The present invention will now be further illustrated by way of the following non-limiting examples, in which parts and percentages are by weight unless otherwise indicated.

EXAMPLES

The present invention is more particularly described in the following examples that are intended as illustrations only, since numerous modifications and variations within the scope of the present invention will be apparent to those of skill in the art. Unless otherwise noted, all parts, percentages, and ratios reported in the following examples are on a weight basis, and all reagents used in the examples were obtained or are available from the chemical suppliers described below or may be synthesized by conventional techniques.

Materials Used

Chemia fragrance/starch powder combination available from Chemia Corporation, St Louis Mo.

Chemia fragrance/SLS powder combination available from Chemia Corporation, St Louis Mo.

Laundry Fresh fragrance available from Arylessence, Marietta, Ga.

Lumulse POE-40—$C_{18}$ 40 moles EO—ethoxylated stearic acid, available from Lambent Technologies Corporation, Gurnee, Ill.

Lumulse POE-100—$C_{18}$ 100 moles EO—ethoxylated stearic acid—available from Lambent Technologies Corporation, Gurnee, Ill.

Tomadol 25-12 a nonionic Alcohol Ethoxylate surfactant made from linear C12-15 alcohol with 11.9 moles (average) of ethylene oxide available from Air products, Inc., Allentown, Pa.

Tomadol 25-7a nonionic Alcohol Ethoxylate surfactant made from linear C12-15 alcohol with 7.3 moles (average) of ethylene oxide, available from Air products, Inc., Allentown, Pa.

Tomadol 25-20 a nonionic Alcohol Ethoxylate surfactant made from linear C12-15 alcohol with 20 moles (average) of ethylene oxide, available from Air products, Inc., Allentown, Pa.

Acusol 445ND a spray dried homopolymer of acrylic acid with a molecular weight of 4500 available from Dow Chemical Company Midland, Mich.

Sipernat 22 a silica with spherical particles, low fines content and high oil absorption (DBP). Available from The Carey Company, Addison, Ill.

Formulations

Fragrance/Starch

| | |
| --- | --- |
| Chemia fragrance starch powder | 40-50 wt. % |
| Tomadol | 20-50 wt. % |
| PEG | 0-40 wt. % |
| Sodium bicarbonate/citric acid | 0-30 wt. % |
| Sipernat 22 | 0-20 wt. % |
| Acusol 445ND | 0-5 wt. % |

Fragrance SLS

| | |
| --- | --- |
| Chemia fragrance SLS | 75-85 wt. % |
| PEG | 0-20 wt. % |
| Lumulose (POE 40 or 100) | 0-20 wt. % |
| Acusol | 0-10 wt. % |

Arylessence/SLS

| | |
| --- | --- |
| Arylessence fragrance SLS | 40-70 wt. % |
| Polyvinyl pyrrolidone | 0-30 wt. % |
| Sipernat 22 | 0-10 wt. % |
| Sodium/bicarbonate/citric acid | 0-30 wt. % |
| Sodium cumene sulfonate | 0-25 wt. % |
| Accusol 445ND | 0-30 wt. % |

The formulations were mixed and 50 grams of sample were placed into a cylindrical punch assembly. The punch assembly was placed in the center of the press plates. The press lever was cranked until 1000 psi was reached and held for 20 seconds. The psi occasionally relaxed to a lower number over time, so small adjustments with the lever to reach 1000 psi were sometimes necessary.

Successful formulations were stable under a range of temperatures, formed a clear use solution upon disintegration, and did not have significant fragrance weep.

Starch Technology

Examples 1-9

The raw materials identified for each of Example 1-9 in Table 1 below were combined and mixed. Each of Examples 1-9 contained Chemia fragrance/starch powder combination mixed with various surfactants, solidifiers, disintegration aids, effervescence components, couplers, and high temp stabilizers.

TABLE A

| | Example 1 | Example 2 | Example 3 | Example 4 | Example 5 | Example 6 | Example 7 | Example 8 | Example 9 |
|---|---|---|---|---|---|---|---|---|---|
| Fragrance/starch | 40% | 40% | 40% | 40% | 40% | 50% | 40% | 40% | 40% |
| Tomadol 25-12 | 10% | 10% | 10% | 10% | 20% | | | | |
| Tomadol 25-7 | 10% | 10% | 10% | 10% | 15% | | | | |
| PEG 4000 | 20% | 20% | 20% | 20% | 25% | | 20% | 20% | 20% |
| Sodium Sulfate powder | 20% | | | | | | | | |
| Sodium Bicarbonate powder | | 20% | | | | | | | |
| PEG 1450 | | | 20% | | | | | | |
| Micro Crystalline Cellulose powder | | | | 20% | | | | | |
| Tomadol 25-20 | | | | | | 50% | 40% | | |
| Lumulse 1820 | | | | | | | | 40% | |
| Lumulse POE 40 | | | | | | | | | 40% |

All raw materials unless otherwise specified were mixed to form a mixture and then placed into a cylindrical punch assembly. The punch assembly was placed in the center of the press plates. The press lever was cranked until 1000 psi was reached and held for 20 seconds. The psi occasionally relaxed to a lower number over time, so small adjustments with the lever to reach 1000 psi were sometimes necessary.

An oven stability test was conducted in which the solids were placed in an oven at 50° C. for seven days to determine the stability of the solids. Visual observations of the solids following the storage period were recorded.

The solids were also diluted with dilution water to form a use solution. The dilution test investigated whether the use solution having approximately 0.3125% by weight fragrance was clear or cloudy. Observations regarding the use solution clarity were recorded. Table B provides the oven test results and the dilution test results.

TABLE B

| | |
|---|---|
| Example 1 | Reduced surfactant load<br>Sodium Sulfate as filler<br>PEG 4000 as solidifying agent<br>PEG 4000 was melted before it was mixed into the system<br>Formula was the consistency of a stiff cookie dough before pressing<br>Formula was pressed<br>Formula is resistant to crumbling once pressed solid is cooled<br>Use solution (0.3125% fragrance) in 5 grain water is cloudy |
| Example 2 | Reduced surfactant load<br>Sodium Bicarbonate as filler<br>PEG 4000 as solidifying agent<br>PEG 4000 was melted before it was mixed into the system<br>Formula was the consistency of a stiff cookie dough before pressing<br>Formula was pressed<br>Formula is resistant to crumbling once pressed solid is cooled<br>Use solution (0.3125% fragrance) in 5 grain water is cloudy |
| Example 3 | Reduced surfactant load<br>PEG 1450 as filler<br>PEG 4000 as solidifying agent<br>PEG 4000 was melted before it was mixed into the system<br>Formula was the consistency of a stiff cookie dough before pressing<br>Formula was pressed<br>Formula is resistant to crumbling once pressed solid is cooled<br>Solid was a little wet coming out of the press but did not leak during pressing<br>Use solution (0.3125% fragrance) in 5 grain water is cloudy |
| Example 4 | Reduced surfactant load<br>Micro Crystalline Cellulose as filler<br>PEG 4000 as solidifying agent<br>PEG 4000 was melted before it was mixed into the system<br>Formula was the consistency of wet sand<br>Formula was pressed<br>Formula is resistant to crumbling once pressed solid is cooled<br>Solid was a little wet coming out of the press but did not leak during the pressing<br>Use solution (0.3125% fragrance) in 5 grain water is cloudy<br>Quite a bit of starch & cellulose settling at the bottom of the beaker after dilution |
| Example 5 | Trying to increase the surfactant load<br>PEG 4000 as solidifying agent<br>PEG 4000 was melted before it was mixed into the system<br>Formula is slightly too soft<br>Formula was pressed<br>Pressed solid was sticking to the punch<br>Formula is resistant to crumbling once pressed solid is cooled<br>Use solution (0.3125% fragrance) in 5 grain water is cloudy |
| Example 6 | Trying to increase surfactant load<br>Trying to solidify with a surfactant instead of PEG<br>Tomadol 25-20 was melted before it was mixed into the system<br>Formula was pressed<br>Formula is resistant to crumbling once pressed solid is cooled<br>Use solution (0.3125% fragrance) in 5 grain water is cloudy |
| Example 7 | Trying to increase surfactant load<br>Trying to solidify with the help of a surfactant in addition to PEG<br>Tomadol 25-20 was melted before it was mixed into the system<br>PEG 4000 was melted before it was mixed into the system<br>Formula was pressed<br>Formula is resistant to crumbling once pressed solid is cooled<br>Use solution (0.3125% fragrance) in 5 grain water is cloudy |

TABLE B-continued

| | |
|---|---|
| Example 8 | Trying to increase surfactant load<br>Trying to solidify with the help of a surfactant in addition to PEG<br>PEG 4000 was melted before it was mixed into the system<br>Formula was pressed<br>Pressed solid is resistant to crumbling<br>Use solution (0.3125% fragrance) in 5 grain water is cloudy |
| Example 9 | Trying to increase surfactant load<br>Trying to solidify with the help of a surfactant in addition to PEG<br>PEG 4000 was melted before it was mixed into the system<br>Lumulse POE 40 was melted before it was mixed into the system<br>Formula was pressed<br>Pressed solid is waxy looking<br>Pressed solid is resistant to crumbling<br>Use solution (0.3125% fragrance) in 5 grain water is cloudy |

SLS Technology

The raw materials identified for each of Examples 10-16 in Table C below were combined and mixed. Each of Examples 10-16 contained Chemia fragrance/SLS powder combination mixed with various surfactants, solidifiers, disintegration aids, effervescence components, couplers, and high temp stabilizers.

TABLE C

| | Example 10 | Example 11 | Example 12 | Example 13 | Example 14 | Example 15 | Example 16 |
|---|---|---|---|---|---|---|---|
| Fragrance/SLS | 75% | 75% | 75% | 75% | 75% | 75% | 75% |
| Fragrance | 5% | 5% | 5% | 5% | 5% | 5% | 5% |
| PEG 4000 | 20% | | | | 15% | | |
| PEG 8000 | | | | | | | 15% |
| Lumulse POE 40 | | 20% | | | | | |
| Lumulse POE 100 | | | 20% | | | 15% | |
| PEG 1450 | | | | 20% | | | |
| Acusol 445ND powder | | | | | 5% | 5% | 5% |

All raw materials unless otherwise specified were mixed to form a mixture and then placed into a cylindrical punch assembly. The punch assembly was placed in the center of the press plates. The press lever was cranked until 1000 psi was reached and held for 20 seconds. The psi occasionally relaxed to a lower number over time, so small adjustments with the lever to reach 1000 psi were sometimes necessary.

An oven stability test was conducted in which the solids were placed in an oven at 50° C. for seven days to determine the stability of the solids. Visual observations of the solids following the storage period were recorded.

The solids were also diluted with dilution water to form a use solution. The dilution test investigated whether the use solution having approximately 0.3125% by weight fragrance was clear or cloudy. Observations regarding the use solution clarity were recorded. Table D provides the oven test results and the dilution test results.

TABLE D

| | |
|---|---|
| Example 10 | PEG 4000 as solidifying agent<br>PEG 4000 was melted before it was mixed into the system<br>Formula was pressed<br>Ribbons of material were being extruded from the bottom of the press when pressure was applied - may not need 1000 psi of pressure<br>Pressed solid is resistant to crumbling<br>Use solution (0.3125% fragrance) in 5 grain water is clear<br>Placing use solution on stability (40° F. & 100° F.) - solutions are stable<br>Placed pressed solid on stability (120° F.) - weeping observed |
| Example 11 | Trying to solidify with Lumulse POE 40<br>Lumulse POE 40 was melted before it was mixed into the system<br>Formula was pressed<br>Ribbons of material were being extruded from the bottom of the press when pressure was applied - may not need 1000 psi of pressure<br>Pressed solid is resistant to crumbling<br>Use solution (0.3125% fragrance) in 5 grain water is clear<br>Use solution (0.3125% fragrance) in 17 grain water is clear<br>Placing use solution on stability (40° F. & 100° F.) - solutions are stable<br>Placed pressed solid on stability (120° F.) - no weeping observed |
| Example 12 | Trying to solidify with Lumulse POE 100<br>Lumulse POE 100 was melted before it was mixed into the system<br>Formula was pressed<br>Ribbons of material were being extruded from the bottom of the press when pressure was applied - may not need 1000 psi of pressure<br>Pressed solid is resistant to crumbling<br>Use solution (0.3125% fragrance) in 5 grain water is clear<br>Placing use solution on stability (40° F. & 100° F.) - solutions are stable<br>Placed pressed solid on stability (120° F.) - weeping observed |
| Example 13 | PEG 1450 as solidifying agent<br>PEG 1450 was melted before it was mixed into the system<br>Formula was pressed<br>Ribbons of material were being extruded from the bottom of the press when pressure was applied - may not need 1000 psi of pressure |

TABLE D-continued

| | |
|---|---|
| | Pressed solid is resistant to crumbling |
| | Use solution (0.3125% fragrance) in 5 grain water is clear |
| | Use solution (0.3125% fragrance) in 17 grain water is clear |
| | Placed pressed solid on stability (120° F.) - no weeping observed |
| Example 14 | Modified Example #10 |
| | Acusol 445ND was added to see if it could dry up some of the fragrance seen weeping from the Example #10 solid at high temperature stability (120° F.) |
| | PEG 4000 as solidifying agent |
| | PEG 4000 was melted before it was mixed into the system |
| | Formula was pressed |
| | Ribbons of material were being extruded from the bottom of the press when pressure was applied - may not need 1000 psi of pressure |
| | Pressed solid is resistant to crumbling |
| | Use solution (0.3125% fragrance) in 5 grain water is slightly hazy |
| | Placed pressed solid on stability (120° F.) - weeping observed |
| Example 15 | Modified Example #12 |
| | Acusol 445ND was added to see if it could dry up some of the fragrance seen weeping from the Example #12 solid at high temperature stability (120° F.) |
| | Trying to solidify with Lumulse POE 100 |
| | Lumulse POE 100 was melted before it was mixed into the system |
| | Formula was pressed |
| | Ribbons of material were being extruded from the bottom of the press when pressure was applied - may not need 1000 psi of pressure |
| | Pressed solid is resistant to crumbling |
| | Use solution (0.3125% fragrance) in 5 grain water is clear |
| | Placed pressed solid on stability (120° F.) - weeping observed |
| Example 16 | Acusol 445ND was added to see if it could dry up some of the fragrance seen weeping from the Formula #36 solid at high temperature stability (120° F.) |
| | PEG 8000 as solidifying agent |
| | PEG 8000 was melted before it was mixed into the system |
| | Formula was pressed |
| | Ribbons of material were being extruded from the bottom of the press when pressure was applied - may not need 1000 psi of pressure |
| | Pressed solid is resistant to crumbling |
| | Use solution (0.3125% fragrance) in 5 grain water is slightly hazy |
| | Placed pressed solid on stability (120° F.) - weeping observed |

Water Soluble Polymer Technology

The raw materials identified for each of Examples 17-18 in Table E below were combined and mixed. Each of Examples 17-18 contained fragrance and water soluble polymers mixed with various surfactants, solidifiers, disintegration aids, effervescence components, couplers, and high temp stabilizers.

TABLE E

| | Example 17 | Example 18 |
|---|---|---|
| SLS powder | 20% | 20% |
| Fragrance | 20% | 20% |
| Polyvinyl pyrrolidone powder | 30% | |
| Polyvinyl alcohol powder | | 30% |
| PEG 4000 | 30% | 30% |

All raw materials unless otherwise specified were mixed to form a mixture and then placed into a cylindrical punch assembly. The punch assembly was placed in the center of the press plates. The press lever was cranked until 1000 psi was reached and held for 20 seconds. The psi occasionally relaxed to a lower number over time, so small adjustments with the lever to reach 1000 psi were sometimes necessary.

An oven stability test was conducted in which the solids were placed in an oven at 50° C. for seven days to determine the stability of the solids. Visual observations of the solids following the storage period were recorded.

The solids were also diluted with dilution water to form a use solution. The dilution test investigated whether the use solution having approximately 0.3125% by weight fragrance was clear or cloudy. Observations regarding the use solution clarity were recorded. Table F provides the oven test results and the dilution test results.

TABLE F

| | |
|---|---|
| Example 17 | PEG 4000 as solidifying agent |
| | PEG 4000 was melted before it was mixed into the system |
| | Formula was pressed |
| | Pressed solid is resistant to crumbling |
| | Use solution (0.3125% fragrance) in 5 grain water is cloudy |
| Example 18 | PEG 4000 as solidifying agent |
| | PEG 4000 was melted before it was mixed into the system |
| | Formula was pressed |
| | Pressed solid is resistant to crumbling |
| | Use solution (0.3125% fragrance) in 5 grain water is cloudy |
| | This particular PVA is not cold water soluble |

Effervescent Technology

The raw materials identified for each of Examples 19-21 in Table G below were combined and mixed. Each of Examples 19-21 contained fragrance and various effervescence components mixed with various surfactants, solidifiers, disintegration aids, couplers, and high temp stabilizers.

TABLE G

| | Example 19 | Example 20 | Example 21 |
|---|---|---|---|
| Fragrance | 20% | 20% | 20% |
| Sipernat 22 powder | 10% | 10% | |
| SLS powder | 50% | 25% | 25% |
| Sodium cumene sulfonate | | 25% | 25% |
| Sodium bicarbonate powder | 10% | 10% | 15% |
| Citric acid powder | 10% | 10% | 15% |

All raw materials unless otherwise specified were mixed to form a mixture and then placed into a cylindrical punch assembly. The punch assembly was placed in the center of the press plates. The press lever was cranked until 1000 psi was reached and held for 20 seconds. The psi occasionally relaxed to a lower number over time, so small adjustments with the lever to reach 1000 psi were sometimes necessary.

An oven stability test was conducted in which the solids were placed in an oven at 50° C. for seven days to determine the stability of the solids. Visual observations of the solids following the storage period were recorded.

The solids were also diluted with dilution water to form a use solution. The dilution test investigated whether the use solution having approximately 0.3125% by weight fragrance was clear or cloudy. Observations regarding the use solution clarity were recorded. Table H provides the oven test results and the dilution test results.

TABLE H

| Example 19 | Formula was pressed<br>Pressed solid is resistant to crumbling<br>Pressed 30 g at 2500 psi, 2000 psi and 1500 psi for 20 seconds<br>All tablets were splitting<br>Use solution (0.3125% fragrance) in 5 grain water is cloudy<br>Sipernat 22 leaves a grit behind in use solution |
|---|---|
| Example 20 | Formula was pressed<br>Pressed solid is resistant to crumbling<br>Pressed 30 g at 1500 psi for 20 seconds<br>Use solution (0.3125% fragrance) in 5 grain water is cloudy<br>Sipernate 22 leaves a grit behind in use solution |
| Example 21 | Formula was pressed<br>Pressed solid is resistant to crumbling<br>Pressed 30 g at 1500 psi for 20 seconds<br>Use solution (0.3125% fragrance) in 5 grain water is clear<br>Placing solid on stability (120° F.) - no weeping observed<br>Formula was dispense tested - did not dispense enough at either cold or hot water |

Other

The raw materials identified for each of Examples 22-23 in Table I below were combined and mixed. Each of Examples 22-23 contained fragrance and various surfactants, solidifiers, disintegration aids, effervescence components, couplers, and high temp stabilizers.

TABLE I

|  | Example 22 | Example 23 |
|---|---|---|
| Fragrance | 20% | 20% |
| SLS powder | 25% | 25% |
| Sodium cumene sulfonate powder | 25% | 25% |
| Sodium citrate powder | 30% |  |
| Acusol 445ND powder |  | 30% |

All raw materials unless otherwise specified were mixed to form a mixture and then placed into a cylindrical punch assembly. The punch assembly was placed in the center of the press plates. The press lever was cranked until 1000 psi was reached and held for 20 seconds. The psi occasionally relaxed to a lower number over time, so small adjustments with the lever to reach 1000 psi were sometimes necessary.

An oven stability test was conducted in which the solids were placed in an oven at 50° C. for seven days to determine the stability of the solids. Visual observations of the solids following the storage period were recorded.

The solids were also diluted with dilution water to form a use solution. The dilution test investigated whether the use solution having approximately 0.3125% by weight fragrance was clear or cloudy. Observations regarding the use solution clarity were recorded. Table J provides the oven test results and the dilution test results.

TABLE J

| Example 22 | Formula was pressed<br>Ribbons of material were being extruded from the bottom of the press when pressure was applied - may not need 1000 psi of pressure<br>Pressed solid is resistant to crumbling<br>Use solution (0.3125% fragrance) in 5 grain water is clear<br>Placing solid on stability (120° F.) - no weeping observed<br>Formula was dispense tested - did not dispense enough at either cold or hot water |
|---|---|
| Example 23 | Formula was pressed<br>Pressed solid is resistant to crumbling<br>Use solution (0.3125% fragrance) in 5 grain water is clear<br>Placing solid on stability (120° F.) - no weeping observed |

What is claimed is:

1. A method of making a solid air freshener comprising the steps of:
    combining a starch based fragrance component, a solidifier and a surfactant, wherein said surfactant and solidifier are in a ratio of greater than 1:1 on a percent weight basis; and
    compressing said components to form a solid,
    wherein said fragrance component, solidifier and said surfactant are held together not by solidification from a melt but by binding through compression.

2. The method of claim 1 wherein said air freshener comprises greater than 10% fragrance.

3. The method of claim 1 further comprising a disintegration aid.

4. The method of claim 1 wherein the surfactant is a polyethylene oxide surfactant.

5. The method of claim 4 wherein said polyethylene oxide surfactant is has a melting point greater than 30° C.

6. The method of claim 5 wherein said surfactant is a C8 to C24 alcohol with from about 20-40 moles of ethoxylate.

7. The method of claim 6 wherein the surfactant is sodium lauryl sulfate.

8. The method of claim 1 wherein said solidifier is polyethylene glycol having an average molecular weight of 4000.

9. The method of claim 1 wherein said starch fragrance component is present in an amount of from about 35-60 wt. %.

10. The method of claim 1 wherein said surfactant is present in an amount of from about 20-50 wt. %.

11. The method of claim 1 wherein said solidifier is present in an amount of from about 15-40 wt. %.

12. The method of claim 1 wherein said compression produces a stable solid with reduced leaching of fragrance.

13. The method of claim 1 wherein said air freshener is stable under a range of temperatures, formed a clear use solution upon disintegration, and did not have significant fragrance weep.

14. A method of deodorizing/freshening a surface, bounded volume of air, or environment, comprising:
- obtaining a pressed solid air freshener composition comprising a fragrance component of from about 40-80 wt. %, a surfactant of from about 20-50 wt. %, and a solidifier of from about 15-40 wt. % wherein, said fragrance component comprises up to about 30% by weight of fragrance, and wherein said fragrance component and said surfactant are held together not by solidification from a melt but by binding through compression;
- dissolving the solid pressed air freshener to form a liquid composition; and
- applying the liquid composition to the surface, bounded volume of air, or environment to eliminate or attenuate odors.

15. The method of claim 14 further comprising the applying a predetermined concentration of the liquid composition for eliminating or attenuating odors.

16. The method of claim 14 wherein said dissolving is by:
- applying water to the solid pressed air freshener so that the air freshener becomes dissolved to form the liquid composition.

17. The method of claim 16 wherein said dissolving occurs within a spray bottle.

18. The method of claim 17 further comprising:
- directing a spray trigger nozzle generally at the surface, bounded volume of air, or environment, and spraying the liquid composition from the spray bottle.

* * * * *